United States Patent [19]

Grubb et al.

[11] Patent Number: 5,432,264
[45] Date of Patent: Jul. 11, 1995

[54] RECOMBINANT 3-DES-OH-CYSTATIN C PRODUCED BY EXPRESSION IN A PROCARYOTIC HOST CELL

[75] Inventors: Anders Grubb; Ake Lundwall; Magnus Abrahamson, all of Lund, Sweden; Henrik Dalboge, Virum, Denmark

[73] Assignee: Novo Nordisk A/S, Bagsvaerd, Denmark

[21] Appl. No.: 929,290

[22] Filed: Aug. 13, 1992

Related U.S. Application Data

[60] Division of Ser. No. 440,221, Nov. 21, 1989, abandoned, which is a continuation-in-part of Ser. No. 297,198, filed as PCT/PK88/00082, May 20, 1988.

[30] Foreign Application Priority Data

May 22, 1987 [DK] Denmark ................... 2609/

[51] Int. Cl.⁶ ............. C12N 15/70; C12N 15/74; C07K 14/81
[52] U.S. Cl. .................. 530/350; 435/69.2
[58] Field of Search ............. 530/350; 435/69.2; 514/12

[56] References Cited

PUBLICATIONS

Grubb et al., 1982, PNAS, 79, 3024–3027.
Brzin et al., 1984, Bioch. Biophy. Res. Comm., 118, 103–109.
Salvesen et al., 1986, Cysteine Proteinases and their Inhibitors, Walter de Gruyter & Co., Berlin, New York, 413–428.
Jacobs et al., 1985, Nature, 313, 806–810.
Abrahamson, M. et al., "Molecular cloning and Sequence . . ." FEBS (1987) pp. 229–233.
Ghiso, J. et al. "Amyloid Fibrils . . ." Proc. Natl. Acad. Sci. U.S.A., (1986) pp. 2974–2978.
Tonelle, C. et al. "Partial Amino Acid . . ." Biochem. & BioPHys. Research Communications (1979) pp. 613–619.
Barett "The Cystatins:a new Class of peptidase . . ." TIBS, (May 1987) pp. 193–196.
Barrett, A. J. et al. Biochem. J. 201:189–198 (1982).
Ghiso, J. et al. Proc. Natl. Acad. Sci. USA 83:2974–2978 (May 1986).
Rijnders, A. W. M. et al. Biochemical and Biophysical Research Communications 132(2):548–554 (Oct. 1985).
Lindahl, P. et al. Biochemistry 27:5074–5082 (1988).
Barrett, A. J. et al. Methods in Enzymology 80:535–561 (1981).
Abrahamson, et al. FEB 06165, 236(1):14–18, Aug. 1988.
Gounaris, A. et al. Biochem J. 1984, 221, 445–452.
Lofberg, H. et al. Scand, J. Clin. Lab. Invest. 39:619–626 (1979).
Lofberg, H. et al. Biomedical Research 2(3):298–306 (1981).

*Primary Examiner*—Garnette D. Draper
*Assistant Examiner*—Sally P. Teng
*Attorney, Agent, or Firm*—Ladas & Parry

[57] ABSTRACT

A recombinant cystatin C polypeptide or a derivative thereof, such as 3-des-hydroxy-cystatin C, is produced biosynthetically by fermentation of a microorganism into which plasmids containing a DNA-sequence coding for said polypeptide have been introduced. Preparations containing recombinant cystatin C, preferably 3-des-hydroxy-cystatin C, have a higher cystein proteinase inhibitor activity than native cystatin C, isolated from human fluids. Such preparations are useful in therapeutic treatments of patients suffering from different diseases, for example herbes simplex.

1 Claim, 5 Drawing Sheets

RECOMBINANT 3-DES-OH-CYSTATIN C PRODUCED BY EXPRESSION IN A PROCARYOTIC HOST CELL

This is a divisional of application Ser. No. 07/440,221 filed on Nov. 21, 1989, now abandoned, which is a continuation-in-part of application Ser. No. 07/297,198 filed Jan. 5, 1989, now abandoned, which is the national stage of application Ser. No. PCT/DK88/00082, filed May 20, 1988.

The present invention relates to a recombinant cystatin C polypeptide and to a DNA-sequence used for biosynthetic expression of the polypeptide. The invention also relates to a method of producing the polypeptide, a plasmid used in the method, a therapeutic preparation containing the polypeptide and a therapeutic treatment in which the preparation is used.

BACKGROUND OF THE INVENTION

Native human cystatin C is known (see ref. 1). It consists, in its naturally occuring form isolated from body fluids, of a mixture of two types of polypeptide, differing in that type I has the N-terminal amino acid sequence: Ser-Ser-OH-Pro-Gly-while type II, called 3-des-OH-cystatin C, has the following N-terminal sequence: Ser-Ser-Pro-Gly-. Thus, the two types only differ in the third amino acid residue. Cystatin C has a useful biological activity as explained in the following. Depending on the origin of the preparations and the extraction method, the activity may vary somewhat.

Cystatin C has 120 amino acids. The amino acid sequence of recombinant 3-des-OH-Cystatin C is as follows Ser-Ser-Pro-Gly-Lys-Pro-Pro-Arg-Leu-Val-Gly-Gly-Pro-Met -Asp-Ala-Ser-Val-Glu-Glu-Glu-Gly-Val-Arg-Arg-Ala-Leu-Asp -Phe-Ala-Val-Gly-Glu-Tyr-Asn-Lys-Ala-Ser-Asn-Asp-Met-Tyr -His-Ser-Arg-Ala-Leu-Gln-Val-Val-Arg-Ala-Arg-Lys-Gln-Ile -Val-Ala-Gly-Val-Asn-Tyr-Phe-Leu-Asp-Val-Glu-Leu-Gly-Arg -Thr-Thr-Cys-Thr-Lys-Thr-Gln-Pro-Asn-Leu-Asp-Asn-Cys-Pro -Phe-His-Asp-Gln-Pro-His-Leu-Lys-Arg-Lys-Ala-Phe-Cys-Ser -Phe-Gln-Ile-Tyr-Ala-Val-Pro-Trp-Gln-Gly-Thr-Met-Thr-Leu -Ser-Lys-Ser-Thr-Cys-Gln-Asp-Ala. Native human cystatin C has been isolated from urine and its amino acid sequence has been determined (see ref 1), after fragmentation of the polypeptide chain, partly using cyanogen bromide and partly using trypsin cleavage. During the analysis it was shown that the amino acid in position 3 (Pro) was hydroxylated to a degree of about 50% but somewhat varied. Cystatin C, in its native form, thus consists of a mixture of two closely related components of almost the same size, the first of which is hydroxylated in position 3 (Pro) while the second (3-des-OH-cystatin C) is not. This fact has not previously been recognized as important and cystatin C has therefore been used and studied in the native form as a mixture.

Cystatin C has now, according to the invention, been separated into the two components and it has surprisingly been shown that the biological effect is solely connected with 3-des-OH-cystatin C.

As is known from literature, cystatin C is an efficient inhibitor for cystein-proteinase, such as papain and cathepsin B. Native human cystatin C has been described by Grubb et al. (ref. 1) who has indicated the amino acid sequence and also described some biological properties.

Cystein-proteinases participate in the intracellular catabolism of proteins and peptides, in the proteolytical conversion of prohormones, in the extracellular degradation of collagen and in the penetration of normal tissue with malignant cells.

As cystatin C and thus also 3-des-OH-cystatin C inhibits cystein-proteinases which accelerate cancer growth or metastasis-formation, it is a potential cancer-inhibiting agent.

Furthermore, cystatin C and thus also 3-des-OH-cystatin C possess antiviral activity. Thus, it is highly effective against herpes simplex virus. In this respect it has a higher activity than the known compound N-benzyloxycarbonyl-leucyl-valyl-glycine diazomethyl ketone (Z-LVG-CHN$_2$ and Acylovir). Preparations containing cysterin C may thus be used in the treatment of herpes simplex.

Cystein-proteinases, e.g. chymopapain, may also be used for treatment of slipped disc. If the cystein-proteinases diffuse into the cerebrospinal fluid, cerebral hemorrhage will occur as a serious side effect of the therapeutic treatment of slipped disc. As cystatin C and thus also 3-des-OH-cystatin C inhibit such side-effect, it has therapeutic use in this connection.

Of specific important is the activity of cystatin C to counteract hereditary cerebral hemorrhage with amyloidosis. In some cases of this disease there has been found deposits of a so-called HCHWA amyloid protein (Refs. 7 and 8). This protein has been shown to be a variant of cystatin C as it lacks the first 10 amino acids of the cystatin C sequence while the amino acid Leu in position 68 of cystatin C, corresponding to position 58 of the HCHWA protein is replaced by the amino acid Glu. It is assumed that this variant of cystatin C has connection to or is responsible for the disease. If this is the case, it may be expected that 3-des-OH-cystatin C would be useful in the treatment of the disease. In the decomposition of collagen in tissue cystein-proteinases participate, and 3-des-OH-cystatin C may therefore probably inhibit such decomposition of tissue.

The cystatin C amino acid sequence isolated from human urine has been characterized and appears to be somewhat homologous to c-Ha-ras oncogene products.

DESCRIPTION OF THE PREFERRED EMBODIMENTS

Figure 1:
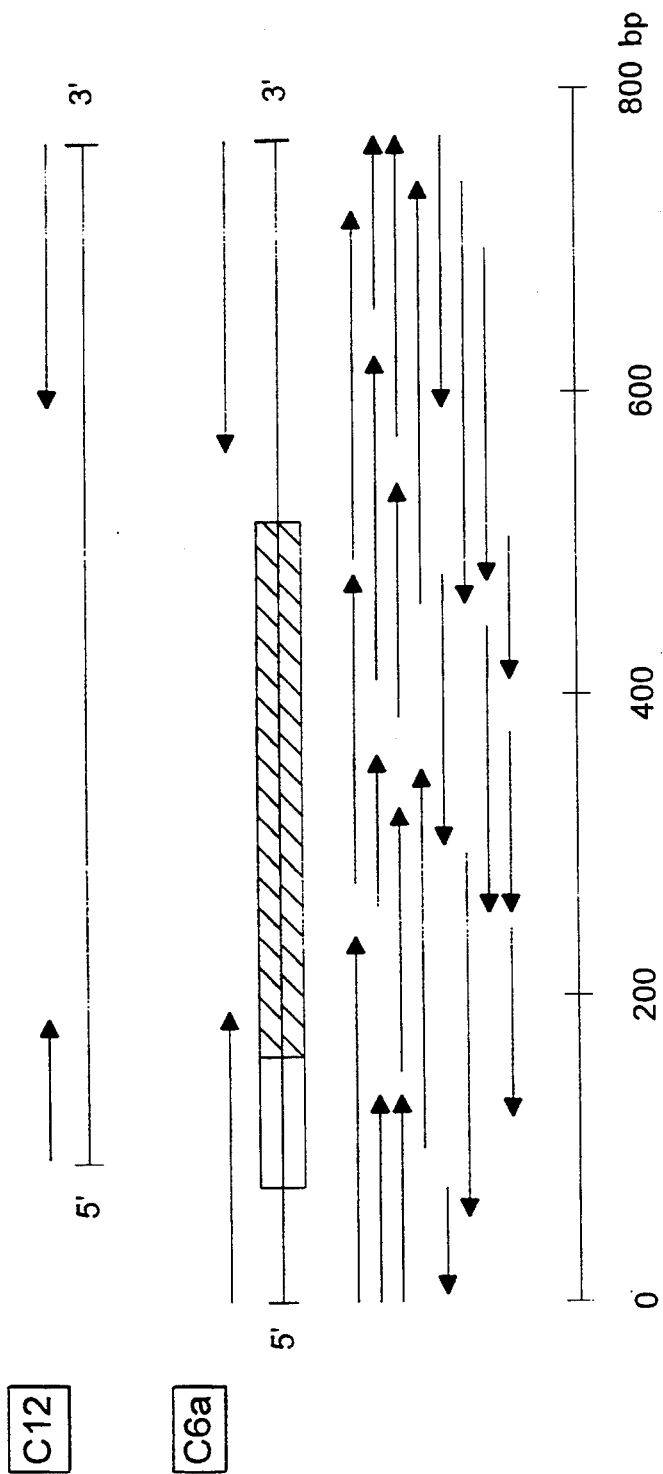
FIG. 1 illustrates a sequencing strategy for recombinant human cystatin C cDNA- inserts

One embodiment of the invention relates to a new DNA sequence coding for 3-des-OH-cystatin C or modifications thereof. The sequence may be a cDNA-sequence formed on the basis of human cells or placenta having a sequence

```
                                                                                                  22
GGGCGCAGGGGTCCTCTCTAT

CTAGTCCAGCCTCTCGCCTGCGCCCCACTCCCCGCGTCCCTAGCCG

95
ACC ATG GCC CCC CTG CGC                                                                           CGC
    Met Ala Pro Leu Arg                                                                           Arg
    -26                                                                                           -21

155
GCC CCG CTG CTC CTG CTG CTG GCC ATC CTG GCC CTG CTG GCC GTG GCC CTG CCC CTG GGC
Ala Pro Leu Leu Leu Leu Leu Ala Ile Leu Ala Leu Leu Ala Val Ala Leu Pro Leu Gly
-20                                                                            -1

215
TCC AGT CCC GGC AAG CCG GCA CTG GCG GCG GTG GAG GAC TTT CAT CCA TGG CCA CAT ACA GAG
Ser Pro Gly Lys Pro Ala Leu Ala Ala Val Glu Asp Phe His Pro Trp Pro His Thr Glu
 1                                                                                                 20

275
GAG GGT CGG CGT GCG GCG GTC GTC GCC CGA CCA CAT GAC CAG CCA CAG ACA GGC GAC
Glu Gly Arg Arg Ala Ala Val Val Ala Arg Pro His Asp Gln Pro Gln Thr Gly Asp
 21                                                                                                40

335
ATG TAC CAC TTC TGC CCC GTG GCT GTA CCC AGC GCC AGC GTA CAG GCC GTG
Met Tyr His Phe Cys Pro Val Ala Val Pro Ser Ala Ser Val Gln Ala Val
 41                                                                                                60

395
AAC TAC TTC TTG CCC TGC CTG ACC AAG ACG CCC AGC AAC AAC TTG
Asn Tyr Phe Leu Pro Cys Leu Thr Lys Thr Pro Ser Asn Asn Leu
 61                                                                                                80

455
GAC AAC TGC CCC GTG CCT CGA CCA GAC CAG CTG AAA AGG TCT TTC CAG
Asp Asn Cys Pro Val Pro Arg Pro Asp Gln Leu Lys Arg Ser Phe Gln
 81                                                                                                100

515
ATC TAC GCT TAC CCT TGG ACA ATG GGC TCG AAA TCC AAA AAA GAC GCC
Ile Tyr Ala Tyr Pro Trp Thr Met Gly Ser Lys Ser Lys Lys Asp Ala
 101                                                                                               120

593
TAG GGGTCTGTACCGGCTGGCCTGTGCTATCACCTCTTATGCACCTCCACCCCCTCTATTCCCACCCTGAC

672
TGGTGGCCCCTGCCTTGGGGAAGGTCTCCCATGTGCCTGCACCAGGAGACAGAGAAGCAGGGGCCTTTC

751
TTGCTCAGCAAGGGGCTCTGCCCTCGCCTCCTTCCTGCTTCTCTCATAGCCCCGGTGTGCGGTGCATACACCCCACC

777
TCCTGCAATAAAATAGTAGCATCCCC
```

Further, the invention relates to modified 3-des-OH-cystatin C, in which one or more amino acids at positions 5-17, and/or 55-59 have been replaced by another amino acid. An example of such modified 3-des-OH-cystatin C is a derivative in which Gly at position 11 is changed to Leu.

In the method of producing biosynthetic 3-des-OH-cystatin C or a modified cystatin C or 3-des-OH-cystatin C, a host organism is used, such as bacterium, a yeast cell or a mammal cell line, in which a vector is introduced, such as a plasmid having the structure suited for expressing the polypeptide desired.

The DNA-sequence in question is inserted together with a signal sequence, promotors etc in a plasmid incorporated in the microorganism which is subsequently cultured in a manner known per se.

In the method according to the invention, a host organism containing the DNA-sequence described is cultured in a substrate, the 3-des-OH-cystatin C formed subsequently being extracted from the culture. The preferred host organism is E. coli, but in principle any microorganism may be used, including yeast cells such as Saccharomyces cerevisiae, or culturing can proceed by means of mammalian cells.

The 3-des-OH-cystatin C formed is extracted from the culture in a manner known per se, e.g. by extraction by way of solvents and purification by chromatography. Affinity chromatography with monoclonal or polyclonal antibodies is particularly suited for isolating 3-des-OH-cystatin C in a pure state.

Isolation and analysis of cDNA clones have been effected by screening recombinant phages. Thus, λgt11 cDNA library from human placenta and liver mRNA have been used. Screening was at a density of 50.000 plaques pr. 130 mm petri-dishes with affinity-purified antibody substance by a method according to Young and Davis. Bound antibody body was demonstrated by alkaline phosphatase-conjugated anti-substance (Promega Bioteknik).

λ-phages produced by the plate lysate method were isolated by centrifugation in a CsCl gradient. DNA was extracted by standard methods. A mixed oligonucleotide probe being specific for 3-des-OH-cystatin C was hybridized to the product of phage DNA reacted with EcoRI in a Southern blot experiment. Hybridized cDNA insertion was ligated in EcoRI-linearized pUC18 plasmid vectors which were then used for transforming E. coli JMB83 cells. Plasmids were produced by alkaline lysis method. DNA sequencing of insertions, the sub-clone in M13mp8, was carried out using a modified di-deoxy-chain terminator technique.

Figure 2:
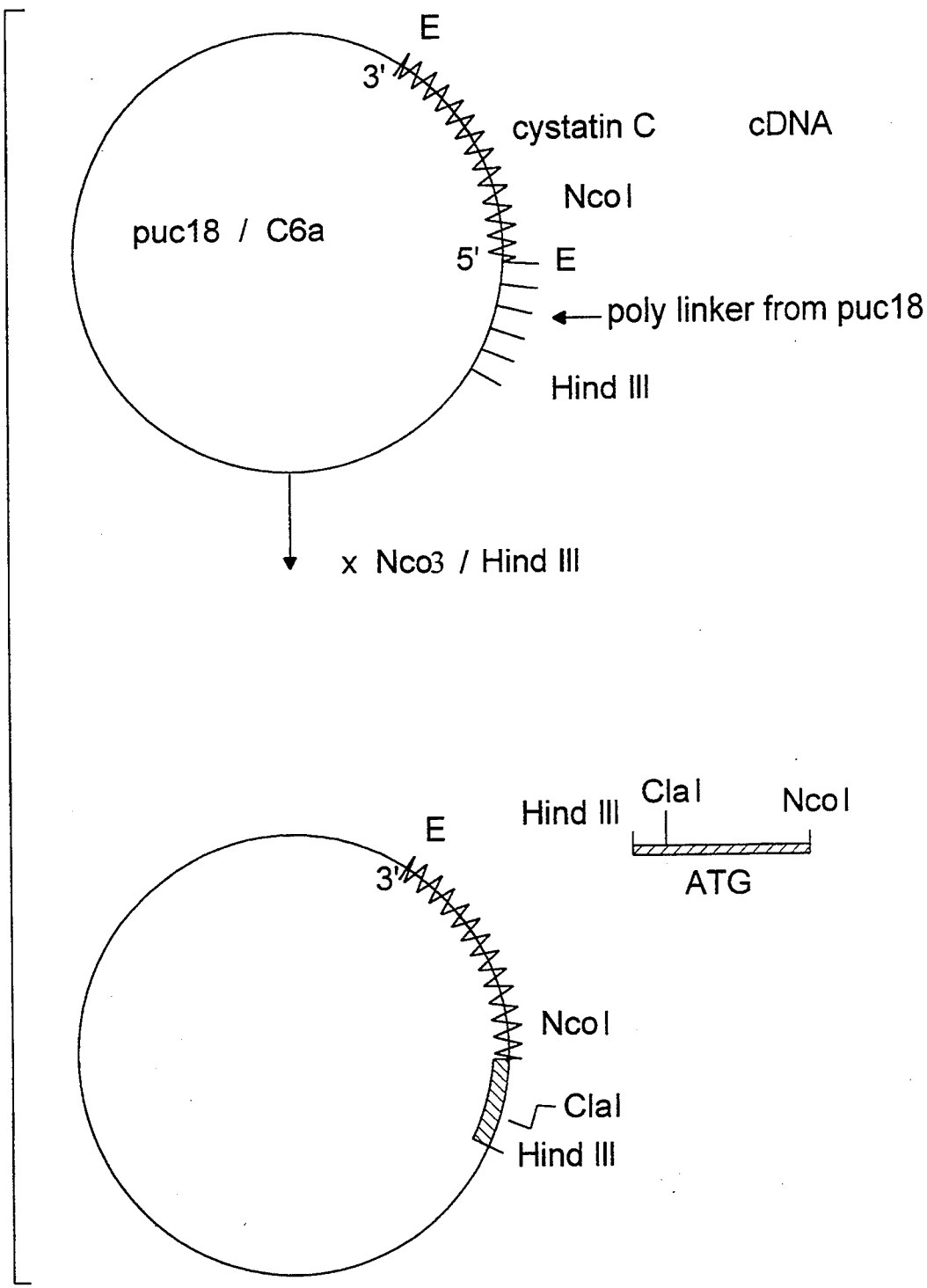
FIG. 2 illustrates the construction of a plasmid from pUCIS/C6a FIG. 3 illustrates the construction of the plasmid pHD262 from pHD162
Figure 3:
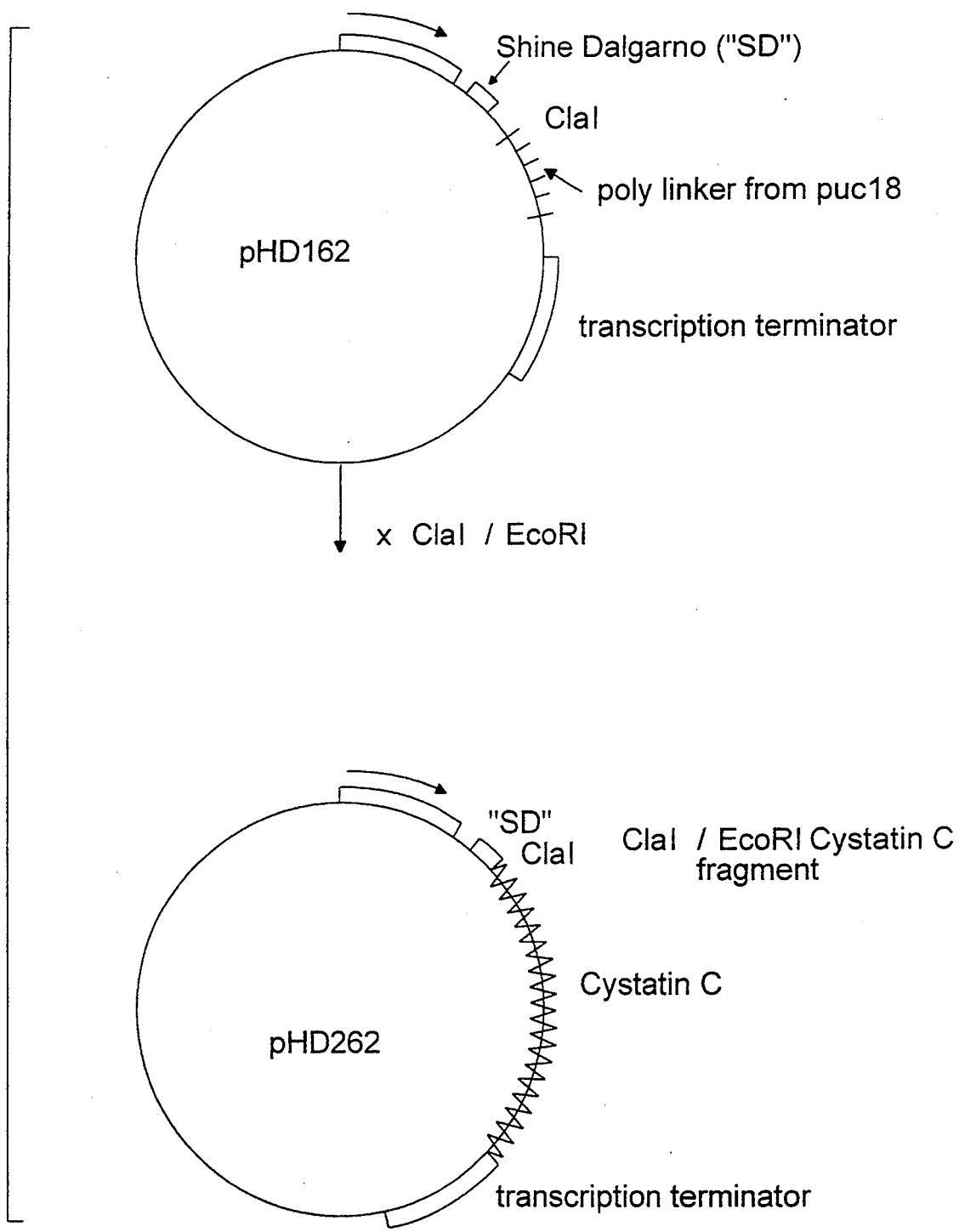
Figure 4:
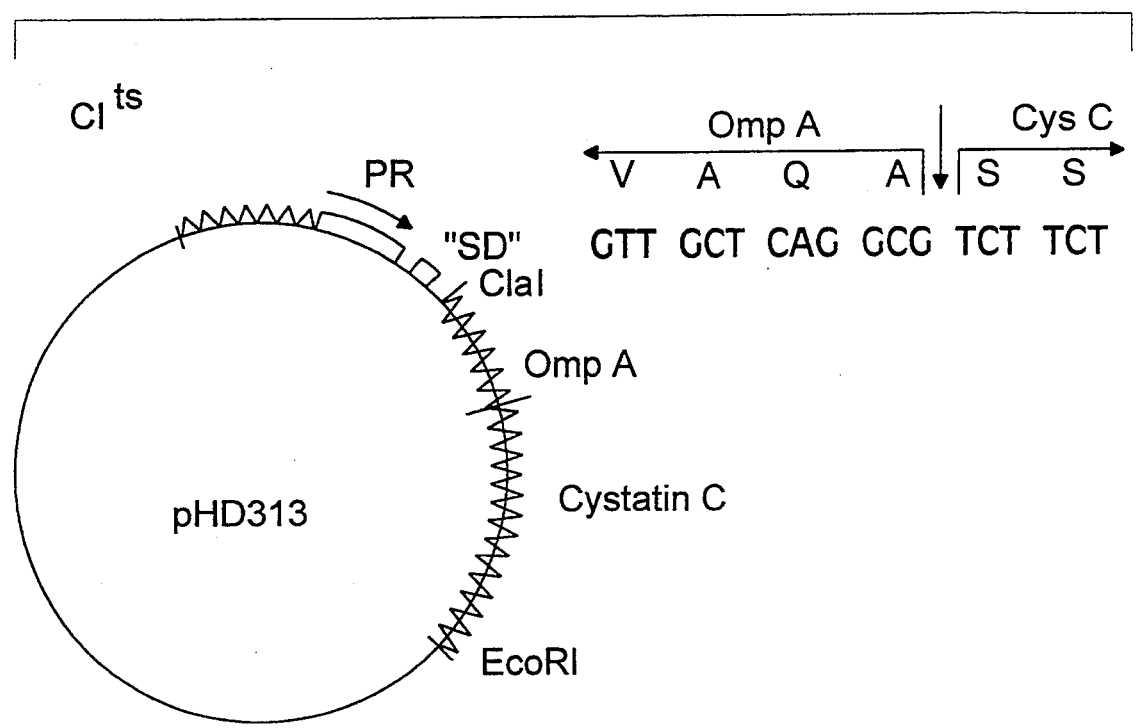
FIG. 4 illustrates the plasmid pHD313
Figure 5:
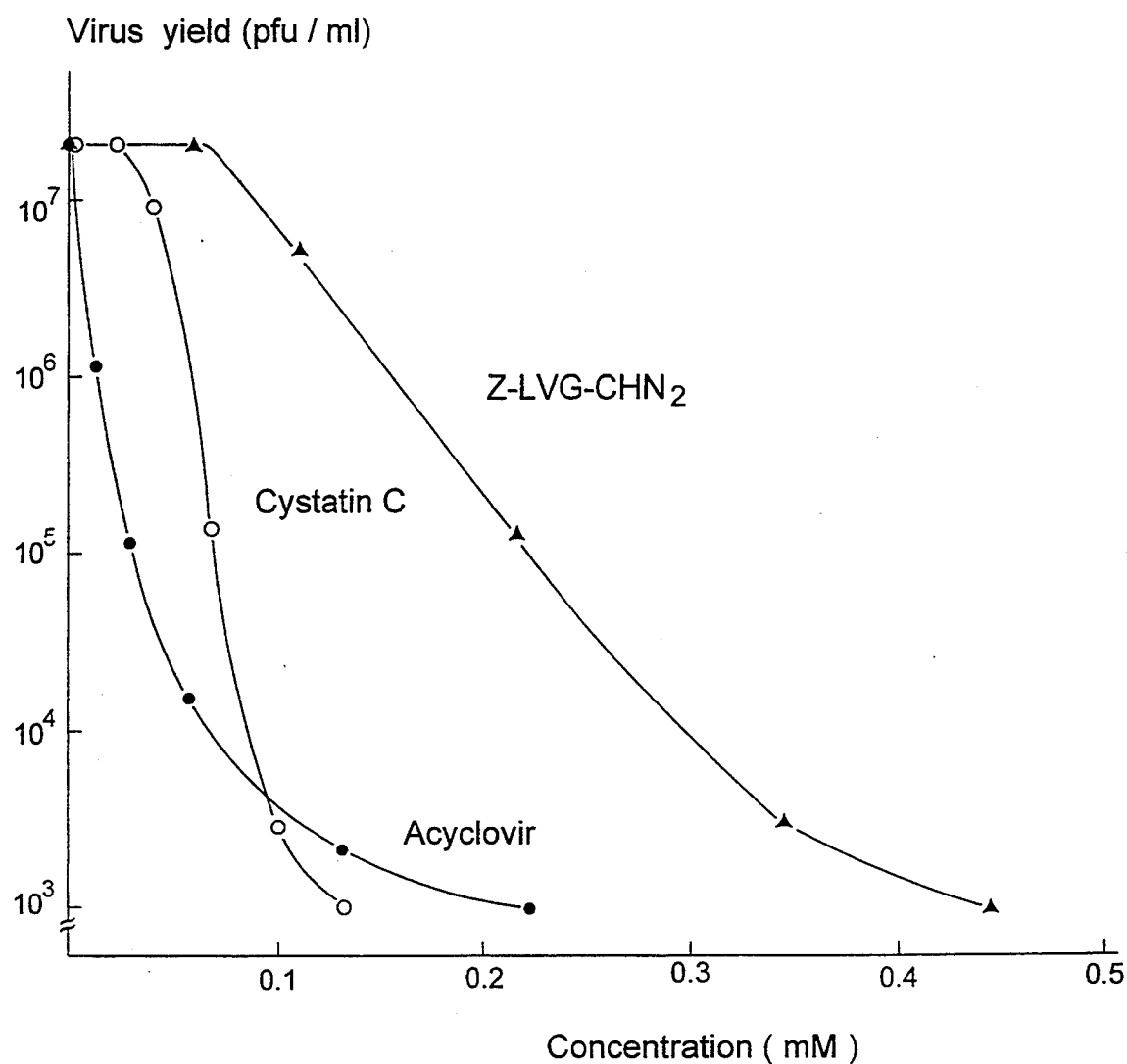
FIG. 5 illustrates the growth curve of herpes simplex virus in the presence of different concentrations of cystatin C and two known antiviral agents.

The invention is further illustrated by way of the following examples, and with reference to the drawing, where FIG. 1 illustrates a sequencing strategy for recombinant human cystatin C cDNA-inserts, FIG. 2-4 illustrate the construction of some plasmids and FIG. 5 shows a diagramme, illustrating the growth curves of herpes simplex virus in the presence of different concentrations of cystatin C and two known antiviral agents.

EXAMPLE 1

Construction of a cDNA coding for cystatin C cDNA library from human liver, prostate and placenta were screened for cystatin C coding clones. About $1.2 \times 10^6$ recombinants from prostata cells were screened with antibodies and a mixed oligonucleotide probe. The result of this screening was negative. On the other hand screening of $6 \times 10^5$ recombinants of placenta cells yielding nine clones which reacted with the antibodies.

Three of these clones, designated C5, C6a and C12 respectively, were used in the following. Their inserts of 800, 800 and 700 base pairs, respectively, were specifically hybridized by Southern blot experiments to a mixed oligonucleotide, constructed from protein-sequence-data.

By sequencing inserts from clones C6a and C12, the subclone in EcoRI-cut M13mp8, it was disclosed that the inserts shared the same 3'-sequence, containing the polyadenylation signal AATAAA.

The entire sequence of both strings of the clone C6a cDNA insert was determined by sequencing randomly ovelapping fragments, the sub-clones in M13mpS. Each nucleotide was determined on an average 5.63 times. Data achieved by sequencing cDNA inserts of clones C6a and C12 from the ends revealed that the sequence of C12 inserts starts at position 91 of the C6a, see FIG. 1.

The C6a insert contains 777 base pairs, including 77 base pairs of 5'-non-coding sequence and 262 base pairs of 3'-non-coding sequence. The polyadenyl signal AATAAA at position 756-761 is succeeded by 15 nucleotides. A possible translation initiation in agreement with the sequence discovered by Kozak is found 6 bp downstream of a stop codon. Initiation at this position and translation stops at the TAG-code at positions 516-518 finally resulted in a 120 amino acid long cystatin C with a signal sequence of 26 amino acid residues. The corresponding protein has the same amino acid sequence as cystatin C, isolated from urine. The activity is substantially higher, however, as explained above and further demonstrated in example 10.

In FIG. 1 is illustrated a sequencing strategy for recombinant human cystatin C cDNA-inserts. Inserts of the clones C12 and C6a were sequenced from their ends by the chain-termination-method. A "shotgun" sequencing-analysis technique was used for sequencing both DNA-strands of C6a inserts. The horizontal arrows indicate the direction and extension of each sequencing analysis. The protein-coding area for inserted C6a is boxed and the hatched part indicates the area which codes for mature protein.

The DNA-structure coding for cystatin C is a nucleotide sequence contained in the nucleotide sequence of the clone C6a cDNA which codes for human pre-cystatin C. The numbering of the nucleotid sequence starts at the first nucleotide and proceeds in the direction from 5' to 3'. The numbering of the amino acid starts with the first amino acid in the mature protein. The Kozak-initiation and the polyadenylation-ring signal are underlined.

Example 2

Cytoplasmatic expression of methionine extended 3-des-OH-cystatin C in E. coli

The plasmid pUC18/C6a containing the cDNA sequence for 3-des-OH-cystatin C was cut by the restriction enzymes NcoI/HindIII, whereafter the plasmid fragment was purified. A synthetic DNA linker containing the code sequence for the amino acid methionine and the approx. first 40 bases of mature cystatin C were subsequently introduced between the NcoI and the HindIII sites (FIG. 2), instead of the codons occurring in the cDNA of 3-des-OH-cystatin C, codons were used in the linker which results in high protein yield in E.

*coli.* This plasmid was cut by the restriction enzymes ClaI/EcoRI, whereafter a fragment of about 600 bp containing the code sequence for methionin-extended 3-des-OH-cystatin C was purified.

The plasmid pHD162 containing a synthetic promotor and Shine and Dalgarno sequence was cut by the restriction enzymes ClaI/EcoRI, whereafter the plasmid fragment was purified. This plasmid fragment was subsequently combined with the above mentioned 600 bp fragment to form the 3-des-OH-cystatin C expression plasmid pHD262 (coding for methionin cystatin C) (FIG. 3). *E. coli* MC1061 containing the above mentioned expression plasmid was cultured as described below.

Example 3

Periplasmatic expression of 3-des-OH-cystatin C in *E. coli*

The plasmid pUC18/C6a mentioned in example 2 was cut by the restriction enzymes NcOI/HindIII, whereafter the plasmid fragment was purified. A synthetic DNA linker containing the code sequence for Outer membrane protein A (OmpA) from *E. coli* and the first approx. 40 bases of mature cystatin C were subsequently inserted between the NcoI and HindIII sites. Optimal *E. coli* codons were used. This plasmid was subsequently cut by the restriction enzymes ClaI/EcoRI, whereafter a fragment of about 700 bp containing the code sequence for the OmpA signal peptide and cystatin C were purified.

The above fragment was then introduced in an expression plasmid containing the λPR promotor, an optimal Shine and Dalgarno sequence, the polylinker region from the plasmid pUC18 and the temperature sensitive CI repressor gene from λ. The plasmid pHD313 (FIG. 4) hereby formed was then introduced in *E. coli* MC1061. The expression of cystatin C and purification of cystatin C were carried out as herein described.

Example 4

Periplasmatic expression of 3-des-OH-cystatin C in *E. coli*

The plasmid pUC18/C6a was cut by ApaI/EcoRI, and a fragment of aprox. 680 base pairs was purified and ligated onto a synthetic ApaI/ClaI linker containing the code sequence for about the first 3 amino acids of pre-3-des-OH-cystatin C. The fragment was subsequently introduced into the expression plasmid, mentioned in example 3, containing the temperature inducing λPR promotor.

Example 5

Expression of periplasmatic modified 3-des-OH-cystatin C in *E. coli*

A HindIII/EcoRI fragment of about 700 bp was isolated from the expression plasmid pHD313 (example 3). The fragment was introduced in M13 MP18 and exposed to in vitro mutagenesis so that the code sequence for cystatin C was changed to contain one or more of the modifications appearing from the following table 1.

After in vitro mutagenesis, a number of clones were cultured and sequences determined. Clones with the desired sequences were subsequently cut by ClaI/Eco RI, whereafter a fragment of about 700 bp was isolated and introduced into the expression plasmid pHD313.

The plasmids hereby formed were cultured, and the product purified as described above.

Table

1. $Gly^{11} \to$ pos. charged, e.g. Arg
2. $Gly^{11} \to$ neg. charged, e.g. Glu
3. $Gly^{11} \to$ strongly hydrofob., e.g. Trp
4. $Gly^{11} \to Ala^{11}$, $5Gly^{11} \to Ser^{11}$
5. Substitution in single amino acids, e.g.
   a.) $Arg^8 \to Gly$
   b.) $Leu^9 \to Arg,Gly$
   c.) $Val^{10} \to Arg,Gly$
   d.) $Gly^{12} \to Arg,Glu$
   e.) $Pro^{13} \to Arg,Glu,Trp$
   f.) $Met^{14} \to Arg,Glu$
6. Substitution of the entire region, e.g. $Arg^8\text{-}Met^{14} \to$ Gly-Gly-Gly-Gly-Gly-Gly-Gly

Example 6

Production of cystatin C on a technical scale by batch fermentation

*E. coli* MC1061 pHD 313-1-1, which expresses 3-des-OH-cystatin C with correct N-terminal, is cultured on LB petri dish containing ampicillin. A single colony is transferred to a 100 ml shaker flask containing LB medium and 50 mg/l ampicillin. This is incubated at 30° C., 200 rpm for 20 hours.

The fermentation is carried out in 10 l laboratory fermentor under the following conditions: pH=7.2, aeration =1VVM, stirring=1000 rpm and temperature=30° C. in the first phase. The medium used consists of yeast extract, casamino acids and various salts.

The fermentor is inoculated with 100 ml culture from the shake flask and the dosing of glucose starts when the biomass concentration is OD525nm=5. The feed rate must be 3.5 g glucose/l/h, and it is maintained throughout the process. The formation of 3-des-OH-cystatin C is induced by raising the temperature in the fermentor to 40° C. in the growth phase (OD525nm=50) 3-des-OH-cystatin C is formed quickly. 2 hours after the temperature was raised the fermentation is ended by lowering the temperature 20° C. and raising pH to 9.0. The entire fermentation process lasts about 12 hours. By the process are achieved final concentrations of 3-des-OH-cystatin C of approx. 1000 mg/l (3-des-OH-cystatin C constitutes aprox. 10% of the total protein in the cell).

Extraction of 3-des-OH-cystatin C

Extraction I of 3-des-OH-cystatin C from *C. coli*:

The cell suspension from the fermentation is centrifuged. The cells are resuspended in 20–25% w/w sucrose, 0.1M EDTA, 0.2M Tris pH 9.0 and agitated for 20 min. Cells are removed by centrifugation and the pellet quickly resuspended in 0° C. 10 mM Tris pH 9 under vigorous agitation for 10 min.

The supernatant herefrom contains 3-des-OH-cystatin C from the periplasmatic phase (70% of total extraction by mechanical homogenization).

Extraction II of 3-des-OH-cystatin C from *E. coli*:

Cell suspension from fermentation is adjusted to pH=10.5 with 5M NaOH. After stirring for 20 min. the suspension is centrifuged. The supernatant herefrom contains 3-des-OH-cystatin C.

Extraction III of 3-des-OH-cystatin C from *E. coli*

Cell suspension from fermentation is centrifuged and resuspended in 0.5M Tris pH=10.5. After stirring for 20 min. the suspension is centrifuged. The supernatant herefrom contains cystatin C.

The extract is dialyzed against 20 nM ethanolamine pH=10.0 with a dialyze membrane of the type Spectropor ® (mw cut 3500) and is then subjected to a Q-Sepharose column equilibrated in 20 mM ethanolamine, pH=10.0. Fractions containing 3-des-OH cystatin C are combined and concentrated on a filter of the type Diaflo ®YM2. Then the material is subjected to a column of the type Bio-Gel ®P60, equilibrated in 0.05M ammonium hydrogen carbonate. Fractions containing 3-des-OH-cystatin C are collected. By this isolation procedure the yield is typically 50–60%.

Example 7

Construction of a synthetic gene coding for 3-des-OH-cystatin C by using optimal E. coli codons It is known from the literature that highly expressed E. coli proteins uses certain codons for expressing the individual amino acids. Simultaneously with the production of cDNA for 3-des-OH-cystatin C, a cystatin C gene was synthesized on the basis of the published amino acid sequence, the gene contained the codons preferred in highly expressed E. coli proteins. The gene was also modified in such a way as to allow a fusion with the signal sequence from either Outer membrane protein A from E. coli or the signal sequence from the fimbriaprotein K88/99 from E. coli. After synthesis, the above mentioned gene was step-cloned in the plasmid pUC18. The gene was hereafter isolated and introduced in the expression plasmid mentioned in example 3 in combination with one of the above mentioned signal sequences. The plasmid was introduced into E. coli MC1061 and cultured as described above.

OmpA-3-des-OH-cystatin C gene with optimal E. coli codons has the following DNA-structure: CCG-ATG-AAA-AAA-ACT-GCT-ATC-GCT-ATC-GCT-GTT-GCT-CTG-GCT -GGT-TTC-GCT-ACT-GTT-GCT-CAG-GCT-TCT-TCT-CCT-GGT-AAA-CCG -CCT-CGT-CTG-GTT-GTT-GGT-CCG-ATG-GAC-GCT-TCT-GTT-GAA-GAA -GAA-GGT-GTT-CGT-CGT-GCT-CTG-GAC-TTC-GCT-GTT-GGT-GAA-TAC -AAC-AAA-GCT-GTT-AAC-GAC-ATG-TAC-CAC-TCT-CGT-GCT-CTG-CAG -GTT-GTT-CGT-GCT-CGT-AAA-CAG-ATC-GTT-GCT-GGT- GTT-AAC-TAC -TTC-CTG-GAC-GTT-GAA-CTG-GGT-CGT-ACC-ACC-TGC-ACC-AAA-ACC -CAG-CCG-AAC-CTG-GAC-AAC-TGC-CCG-TTC-CAC-GAC-CAG-CCG-CAC -CTG-AAA-CGT-AAA-GCT-TTC-TGC-TCT-TTC-CAG-ATC-TAC-GCT-GTT -CCG-TGG-CAG-GGT-ACC-ATG-ACC-CTG-TCT-AAA-TCT-ACC-TGC-CAG -GAC-GCT-TAA-TAG-

Example 8

Production and isolation of 3-des-OH-cystatin C

Bacteria media containing 3-des-OH-cystatin C were centrifuged and bacteria-free media concentrated on a Diaflo TM YM 2 filter. The concentrated, material was dialyzed against 20 mM ethanol amine, pH 10.0 in Spectrapor TM dialysis membrane (mw cutoff 3,500) and subsequently applied to a Q-Sepharose TM column equilibrated in 20 mM ethanol amine, pH 10.0. Fractions containing 3-des-OH-cystatin C were pooled and concentrated on a Daflo TM YM 2 filter. The material was then applied to a Bio-Gel TM column equilibrated in 0.05M ammonium bicarbonate. Fractions containing 3-des-OH-cystatin C were combined. By this isolation procedure the 3-des-OH-cystatin yield is typically 50–60%.

Example 9

Characterization of 3-des-OH-cystatin C 3-des-OH-cystatin C isolated as described above from culture of pHD 313-transformed E. coli, was physically-chemically characterized with a view to biological activity. The results from the characterization were compared with result from corresponding analysis of human cystatin C.

Analysis with Ouchterlony's double immune diffusion technique showed that all cystatin C-epitopes recognized by a polyclonal anti-serum raised against human cystatin C are also present in 3-des-OH-cystatin C. Agarose gel electrofores at pH 8.6 and SDS-PAGE under reducing or non-reducing conditions showed that 3-des-OH-cystatin C and human cystatin C have the same charge and molecular weight. Amino acid analysis showed that the amino acid composition in the produced 3-des-OH-cystatin C also has the same N-terminal sequence.

The following amino acid sequence SSPGKPPRLVGGPMDASVEEEGV-ALDAV-GEYNKASNDMY was found in the biosynthetic 3-des-OH-cystarin C and shown to be identical with that found in human cystatin C (cf ref 1) except that 100%, of the proline residue at position 3 in 3-des-OH-cystatin C lacked a hydroxyl group. Amino acid analysis of disulfide bound peptides showed that 3-des-OH-cystatin C has disulfide bridges between $Cys^{73}$–$Cys^{83}$ and $Cys^{7\text{-}3}$–$Cys^{83}$, i.e. the same as is the case in human cystatin C (cr. ref. 15).

Investigation of the biological activity of 3-des-OH-cystatin C

Biological activity of 3-des-OH-cystatin C was determined through titration against concentration determined papain. The strength of binding 3-des-OH-cystatin on the cystein proteinases papain (EC 3.4.22.2), cathepsin B (EC 3.4.22.1) and dipeptidyl peptidases I (F.C 3.4.14.1) was determined. The equilibrium constant for dissociation of 3-des-OH-cystatin C enzyme complex (0.005 nM, 0.50 nM and 3.1 nM) was within the experimental error limit identical with the equilibrium constant for human cystatin C enzyme complex (<0.005 nM, 0.27 nM and 6.3 nM For papan, cathepsin B and dipeptidyl peptidases I, respectively). Thus, physical-chemical characterization and analysis performed demonstrate that the interaction of 3-des-OH-cystatin C has full biological activity and is identical with human cystatin C with the exception that it lacks hydroxyl groups on residue 3.

Example 10

Comparison of the biological activity of 3-des-OH-cystatin C to cystatin C of human origin The papain-inhibiting capacity of recombinant 3-des-OH-cystatin C was compared with the corresponding activity of human cystatin C.

The human cystatin C was isolated from urine of patients with mixed glomerular-tubular proteinuria by ultrafiltration, ion-exchange chromatography and gel filtration as described in literature (ref. 2,3) and lyophilized. A total of ten different preparations of human cystatin C and 3-des-OH-cystatin C were tested for their cystein proteinase inhibitory capacity. The cystatin C and 3-des-OH-cystatin C preparations derived from human urine and recombinant technique, respectively, were individually dissolved in 0.15 mol/l ammonium bicarbonate. Cystatin C concentrations of the resulting solutions were determined by phys-ico-chemical and immuno-diffusion and quantitation of amino acids released at hydrolysis in 6 mol/l HCl). The cysteine proteinase inhibiting capacities of these solutions were determined by adding them to a solution of isolated papain (cf. ref. 4), a plant cysteine proteinase widely used as a model for cysteine proteinases in general, and then determining the residual proteolytic activity of the resulting mixtures.

The cysteine proteinase activities of the papain solution and the cystatin C-papain mixtures were determined using the fluorogenic substrate Z-Phe-Arg-NHMec (ref. 5). The molar concentration of active enzyme in the papain solutions was determined using the irreversible papain inhibitor E-64 (ref. 6).

The molar inhibitory capacities of the different preparations of cystatin C were then calculated as a ratio between papain-inhibiting capacity of the cystatin C solutions, assuming that one mol of cystatin C inhibits one mol of papain, and the molar concentration of cystatin C in the solutions as measured by physicochemical and/or immunochemical methods and assuming a molecular weight of 13,343 for cystatin C. Measured in this way, the molar inhibitory capacity of cystatin C isolated from human urine ranged from 5–55% while the inhibitory capacity of several samples of recombinant 3-des-OH-cystatin C ranged from 83–98%, showing that the biological potency of all investigated preparations-of recombinant 3-des-OH-cystatin C considerably exceeds the biological potency of all cystatin C preparations isolated from human biological fluids.

Example 11

Therapeutic use of recombinant 3-des-OH-cystatin C as a CNS-protective agent at chymopapain treatment of sciatica Just before chymopapain treatment of patients with sciatica, a molar amount of 3-des-OH-cystatin C three times higher than the molar amount of chymopapain to be used is injected into the cerebrospinal fluid. For example, if 8 mg of chymopapain (the active component of the currently available drugs: Discase ®; Travenol Laboratories Ltd., Thetford, UK and Chymodiactin ® Smith Laboratories, Inc , Rosemont, Ill., U.S.A.) is to be used for intradiscal injection, 12 mg of 3-des-OH-cystatin C is injected into the cerebrospinal fluid. The preparation might be composed of 5 mg 3-des-OH-cystatin C per ml of sterile physiological saline. This will protect against any side effects due to proteolytic breakdown of nervous tissue caused by improper injection of chymopapain into the cerebrospinal fluid.

Alternatively, if clinical or radiographic signs of improper chymopapain injection into the cerabrospinal fluid are observed at, or after, execution of the intended intradiscal chymopapain injection, a molar amount of 3-des-OH-cystatin C three times higher than the molar amount of chymopapain used, is immediately injected into the cerebrospinal fluid in order to inhibit the tissue-damaging effect of chymopapain.

Directly after the injection of 3-des-OH-cystatin C, the patient is gently moved in a way which brings about a rapid distribution of the injected solution of 3-des-OH-cystatin C with the cerebrospinal fluid of the patient.

Example 12

Therapeutic use of 3-des-OH-cystatin C in treatment of Herpes simplex

Preparations containing recombinant 3-des-OH-cystatin C, produced in accordance with the invention, were compared as to antiviral activity with the known antiviral medicaments Cyclovir ® and Z-LVG-CHN$_2$.

In a first set of experiments, paper discs were impregnated with Z-LVG-CHN$_2$ (24 μg per disc) and placed on monolayers of green monkey kidney cells infected with poliovirus type 1 or herpes simplex virus type 1 (HSV).

In this screening for antiviral activity, no inhibition of plaque formation was observed with poliovirus. However, marked inhibition zones occurred around the discs when cells were infected with HSV. Then it was investigated whether the addition of Z-LVG-CHN$_2$ to the cultivation medium could influence growth of poliovirus or HSV in cell cultures. Also in this case HSV replication was blocked (>99.9 inhibition) whereas the effect on poliovirus replication was hardly significant (Table 2).

Human recombinant cystatin C was then tested for antiviral activity against these two viruses and was found to be a potent inhibitor of HSV replication but with no influence on the replication of poliovirus (Table 2). The anti-HSV potencies of cystatin C and Z-LVG-CHN$_2$ were then compared to each other and to that of Acyclovir ® (Welcome) by investigation of dose response curves.

FIG. 5 illustrates growth curves of herpes simplex virus type

TABLE 2

| Anti-viral Activities of 3-des-OH-cystatin C and Z-LVG-CHN$_2$ ||||
|---|---|---|---|
| | Virus Yield (pfu/ml) ||||
| Virus | Medium | 3-des-OH-cystatin | Medium with 1% DMSO | Z-LVG-CHN$_2$ in 1% DMSO |
| Poliovirus type 1 | $1.2 \times 10^8$ | $1.1 \times 10^8$ | $1.5 \times 10^8$ | $4.8 \times 10^7$ |
| HSV type 1 | $8.8 \times 10^7$ | $2.4 \times 10^3$ | $6.4 \times 10^6$ | $1.4 \times 10^3$ |

Methods. Green monkey kidney cells (strain GMK-AH1) were infected with poliovirus (Mahoney strain) or HSV type 1 (F strain) at a multiplicity of 1 and 10, respectively. After 2 hrs attachment serum free medium (MEM, Flow Laboratories) was adjusted to contain 0.10 mM cystatin C or 0.4 mM Z-LVG-CHN$_2$. Z-LVG-CHN$_2$ was dissolved in MEM medium containing 1% dimethyl sulfoxide (DMSO) to keep the peptide derivative in solution. Cells were incubated for 48 hrs at 37° C. followed by freezing and thawing. Plaque titrations (pfu: Plaque-forming units) were performed on GMK-AH1 cells as previously described (19). In all assays three Petri dishes (Falcon: 6 cm diameter) were used per dilution step. Values are given from counts of at least 40 pfu and the values given in the Table are from typical and reproducible experiments.

1 in the presence of different concentrations of Cystatin C, Z-LVG-CHN$_2$ and Acyclovir ®. In the method, CMK-AH1 cells were inoculated with 10 pfu (plaque forming units) per cell, corresponding to $5 \times 10^6$ pfu per ml for 1 hr at 37° C. After washing a residual infectivity of about $10^3$ pfu was recorded and this value thus represents zero time background levels of the growth curves. At this time, serum free medium (MEM) containing different concentrations of the inhibitors was added to the HSV infected cells followed by incubation at 37° C. for 48 hrs. Finally, cells were freeze thawed and plaque titrations were performed. The concentration of 3-des-OH-cystatin C required for inhibition of viral replication to background levels was about 0.13 mM while the corresponding concentrations for Z-LVG-CHN$_2$ and Acyclovir were 0.44 mM and 0.22 mM, respectively. Thus, the anti-HSV potency of both recombinant cystatin C and the peptide derivative, Z-LVG-CHN$_2$, mimicing part of its proteinase-binding centre, is of the same order of magnitude as that of Acyclovir.

In the experiments described above, 3-des-OH cystatin C and Z-LVG-CHN$_2$ were added to the medium after the cells had been incubated with the viruses and then carefully washed. As the inhibitors were not present during this first step. They seem to interfere with later event of importance to HSV replication. This was also demonstrated when Z-LVG-CHN$_2$ (0.40 mM) was mixed with a diluted HSV suspension and present only during the 2 hours of viral adsorption to the cells. In this case the number of plaques was not reduced. Finally, inhibition of HSV replication was not restricted to monkey kidney cells.

Literature

1. Grubb, A & Löfberg, Lt: Proc. Natl. Acad. Sci. 79, 3024–3027, 2982.
2. Löfberg H & Grubb A (1979) Scand J Clin Lab Invest 39, 619–626.
3. Löfberg H, Grubb A & Brun A (1981) Biomed Res, 298–306.
4. Lindahl P, Alriksson E, Jörnvall H & Björk I (1988) Biochemistry 28: 5074–5082).
5. Barrett A J & Kirschke H (1982) Methods Enzymol 80, 535–561.
6. Barret A J, Kembhavi A A, Brown M A, Kirschke H, Knight C G, Tamai M & Hanada K (1982) Biochem J 201, 189–198).
7. Ghiso, J. et al , Proc Natl Acad. Sci. USA, 83:2974–2978 (May 1986).
8. Rijnders, A.W.M. et al., Biochemical and Biophysical Research Communications 132(2): 548–554 (October 1985).

We claim: b 54328034.001

1. An isolated and purified polypeptide 3-des-OH-cystatin C having cystatin C activity produced by culturing a procaryate host cell containing DNA coding for said polypeptide wherein the amino acid sequence of the polypeptide 3-des-OH-cystatin C is:

```
1            5                    10
Ser—Ser—Pro—Gly—Lys—Pro—Pro—Arg—Leu—Val—Gly—

14  15              19
Gly—Pro—Met—Asp—Ala—Ser—Val—Glu—Glu—Glu—Gly—

24           28  29              33
Val—Arg—Arg—Ala—Leu—Asp—Phe—Ala—Val—Gly—Glu—

38           42  43
Tyr—Asn—Lys—Ala—Ser—Asn—Asp—Met—Tyr—His—Ser—

47                52
Arg—Ala—Leu—Gln—Val—Val—Arg—Ala—Arg—Lys—Gln—

56  57          61                    66
Ile—Val—Ala—Gly—Val—Asn—Tyr—Phe—Leu—Asp—Val—

70  71          75
Glu—Leu—Gly—Arg—Thr—Thr—Cys—Thr—Lys—Thr—Gln—

80              84  85
Pro—Asn—Leu—Asp—Asn—Cys—Pro—Phe—His—Asp—Gln—

89              94              98  99
Pro—His—Leu—Lys—Arg—Lys—Ala—Phe—Cys—Ser—Phe—

103                 108
Gln—Ile—Tyr—Ala—Val—Pro—Trp—Gln—Gly—Thr—Met—

112 113             117
Thr—Leu—Ser—Lys—Ser—Thr—Cys—Gln—Asp—Ala.
```

* * * * *